United States Patent
Mulqueen et al.

(10) Patent No.: US 9,109,220 B2
(45) Date of Patent: Aug. 18, 2015

(54) ENVIRONMENTAL REMEDIATION MATERIAL

(75) Inventors: Daniel W. Mulqueen, Denver, CO (US); James L. Fournier, Nicasio, CA (US); Thomas B. Reed, Barre, MA (US)

(73) Assignee: ECI Research and Development Company, Daytona Beach Shores, FL (US)

( * ) Notice: Subject to any disclaimer, the term of this patent is extended or adjusted under 35 U.S.C. 154(b) by 1013 days.

(21) Appl. No.: 13/160,455

(22) Filed: Jun. 14, 2011

(65) Prior Publication Data

US 2011/0306115 A1  Dec. 15, 2011

Related U.S. Application Data

(60) Provisional application No. 61/354,609, filed on Jun. 14, 2010.

(51) Int. Cl.
| | | |
|---|---|---|
| *B01J 20/22* | (2006.01) | |
| *C12N 11/02* | (2006.01) | |
| *B01J 20/20* | (2006.01) | |
| *B01J 20/30* | (2006.01) | |
| *C02F 3/34* | (2006.01) | |
| *C02F 1/28* | (2006.01) | |
| *C02F 3/00* | (2006.01) | |
| *C02F 101/32* | (2006.01) | |

(52) U.S. Cl.
CPC ............ *C12N 11/02* (2013.01); *B01J 20/20* (2013.01); *B01J 20/3078* (2013.01); *B01J 20/3085* (2013.01); *C02F 1/288* (2013.01); *C02F 3/343* (2013.01); *C02F 1/283* (2013.01); *C02F 2003/003* (2013.01); *C02F 2101/32* (2013.01)

(58) Field of Classification Search
CPC .................................. B01J 20/22; C01B 31/08
USPC ........ 600/141–142, 201–249; 403/52–55, 79, 403/91, 112–113, 116; 502/401, 416, 417, 502/526
See application file for complete search history.

(56) References Cited

U.S. PATENT DOCUMENTS

| | | | |
|---|---|---|---|
| 5,110,785 A | 5/1992 | Reed et al. | |
| 5,585,319 A | 12/1996 | Saitoh et al. | |
| 6,326,070 B1 | 12/2001 | Södergren | |
| 7,470,725 B2 | 12/2008 | Schwertfeger et al. | |
| 7,544,635 B2 | 6/2009 | Liang et al. | |
| 8,070,855 B2 * | 12/2011 | Strickland | ........................ 95/141 |
| 2004/0167019 A1 | 8/2004 | Liang et al. | |
| 2009/0255176 A1 | 10/2009 | Giovannetti | |

OTHER PUBLICATIONS

International Preliminary Report on Patentability and Written Opinion dated Dec. 14, 2012.
International Search Report and Written Opinion dated Feb. 28, 2012.

* cited by examiner

*Primary Examiner* — Edward Johnson
(74) *Attorney, Agent, or Firm* — Dietze and Davis, P.C.; Glenn H. Lenzen

(57) ABSTRACT

An environmental remediation material and method for making the same which include processing an organic material to increase the internal surface and surface pore area thereof through pyrolysis, coating the pyrolyzed material with a non-polar substance to enhance the material's oleophilicity, and applying secondary processing treatments designed to optimize the material for preselected chemical remediation applications. The remediation material is insoluble in aqueous environments, free of environmentally hazardous chemicals or compounds and readily transportable and disposable following use.

9 Claims, No Drawings

ENVIRONMENTAL REMEDIATION MATERIAL

CROSS REFERENCE TO RELATED APPLICATIONS

This application claims the benefit of U.S. Provisional Patent Application No. 61/354,609 filed Jun. 14, 2010, which is incorporated herein by reference in its entirety as if fully set forth herein.

FIELD OF THE INVENTION

The present invention relates to a novel composition of matter having application for the removal, remediation, or sequestration of chemical contaminants from other liquids and the method for its manufacture and processing. More specifically, the present invention relates to a novel composition of matter and the method for its manufacture and processing for the removal, remediation, or sequestration of hydrocarbons and petroleum products, and in particular, oil, from water and other liquids having physical and chemical properties similar to those of water.

BACKGROUND OF THE INVENTION

Many attempts have been made to create a material with high absorption/adsorption capacity, including the creation of oleophilic and hydrophobic materials which will preferentially absorb oils and oil-like compounds over water. As used herein, absorption refers to the process of taking something in through pores or interstices, and adsorption refers to the accumulation of gases, liquids or solids on the surface of a solid or liquid. A specific example of such a material and its associated manufacturing process is disclosed in U.S. Pat. No. 5,110,785 issued May 5, 1992 to Reed et al. for "Composition of Matter and Method of Making" (the '785 patent"). Reed and his colleague disclose a process in which material is heated to a temperature between 280° C. and 380° C. for approximately 10 minutes to create a hydrophobic particle capable of floating on water for extended periods of time and which can absorb up to 3.5 times its own weight in oil. However, due to the low temperature and short heating time inherent in the process cycle of the '785 disclosure, the resultant material has a relatively small internal surface area which substantially limits its absorption/adsorption capacity. Similarly, the resultant material as described has not been brought to substantially high carbon content to be made inorganic or biologically unavailable.

Other efforts have focused upon the use of activated carbon for such remediation efforts due to its high internal surface area and ability to absorb/adsorb large amounts of a chemical substance. However, activated carbon does not preferentially select oil over water so that an activated carbon used in an environment with both non-polar and polar molecules will absorb polar molecules readily, thereby decreasing its effectiveness for oil removal. Moreover, activated carbon must be produced and/or regenerated at high temperatures under special conditions, thereby rendering it expensive to produce, especially at small scale.

More recently, U.S. Pat. No. 7,470,725 issued Dec. 30, 2008 to Schwertfeger et al. for "Organically Modified Aerogels" discloses a method for making surface-modified aero gels for use in the afore-mentioned and other applications. However, synthetic materials may not be left safely in the environment without risk that they will contribute to further contamination thereof, and accordingly, afford less than optimal solutions to the environmental contamination problem. Additionally, the production of said aero gel-s requires the use of strong acids and bases, which present an additional hazard in waste disposal.

U.S. Pat. No. 6,326,070 issued Dec. 4, 2001 to Sodergren for "Absorption Means" discloses a method for removing terpene content from sawdust and coating the sawdust with Teflon. The coating of the particle with Teflon increases oil absorption capacity while making the particle hydrophobic. However, because the material does not undergo pyrolysis, the total absorptive capacity is not increased. Moreover, because the particle is coated in polytetrafluoroethylene, it cannot be safely left in the environment or incinerated without releasing fluorine into the environment.

U.S. Pat. No. 5,585,319 issued Dec. 17, 1996 to Saitoh et al. for "Process For Preparing Oil Sorbent And Device For Continuously Making The Same" discloses a method similar to the method disclosed by Reed et al. in the '785 patent. Saitoh et al. disclose a material preparation process and apparatus wherein material is heated to a temperature in the range of 250°-400° C. and then cooled to condense pyrolysates into the resultant char.

U.S. Pat. No. 7,544,635 issued Jun. 9, 2009 to Liang et al. for "Process for Changing Hydrophilic/Hydrophobic Characteristics" discloses a method for producing a material with modified hydrophilic/hydrophobic characteristics by pretreating a biomass sample by soaking in water, alkaline/acidic reagents, expanding agents, or by freezing. The material is then oxidized in either air or a more powerful oxidizing atmosphere such as oxygen, ozone, or hydrogen peroxide. This method differs from the method of the present invention in a number of meaningful ways, the first being that the material is chemically pre-treated before undergoing pyrolysis rather than being treated in the cooling phase after pyrolysis. This is important because moisture in the reaction increases the need for external energy to drive the reaction. Secondly, in the process of the '635 patent, the material is reacted in an atmosphere having an oxidation number at least as high or higher than atmospheric air. The process described herein, however, reacts the material in an environment with an oxidation number below that of atmospheric air. Advantageously, having a lower oxidation number atmosphere reduces the carbon lost from a parent material in pyrolysis, resulting in a higher yield of material and a generally more hydrophobic product.

In view of the foregoing, it is apparent that a need exists for a new and useful material which is well suited for the removal, remediation, or sequestration of oil and oil-like chemicals from water and which can be used to repair environmental damages caused by such chemicals.

SUMMARY OF THE INVENTION

It is an object of the present invention to provide a method for the creation of a novel composition of matter or material which is created through the pyrolysis of a biomass particle under special conditions and subsequent treatment to create specific properties for the removal or sequestration of oil from water or other chemical contaminant remediation.

Another object of the present invention is to provide a method for increasing the absorptive properties and oleophilicity of an organic material.

Another object of the present invention is to provide a novel composition of matter or material which can be treated to a preselected specific density and which may be modified by the addition of chemical or microbial agents to enhance the material's ability to break down chemical compounds and repair environmental damage such as oxygen depletion and other damage caused by oil and oil-like chemical contamination.

Yet another object of the present invention is to provide an effective method for chemical cleanup and environmental remediation with minimal secondary effects upon a targeted ecosystem.

These and other objects, advantages and novel features of the present invention will become apparent from the following description of the invention and appended claims.

DESCRIPTION OF THE PREFERRED EMBODIMENTS

It should be noted that the present description is by way of instructional examples, and the concepts presented herein are not limited to use or application with any single method and/or apparatus for the production of a contaminant remediation material. Hence, while the details of the innovation described herein are for the convenience of illustration and explanation with respect to exemplary embodiments, the principles disclosed may be applied to other types and applications of the production of high absorption/adsorption materials and remediation methods without departing from the scope hereof.

The Method for Creating Environmental Remediation Material:

The initial steps required to create the novel composition of matter herein described having increased absorptive properties and oleophilicity, an organic material or biomass must be heated sufficiently to create a large internal surface area and surface pore area, ideally over 100 $m^2$ per gram and up to 1,500 $m^2$ per gram. The increase in surface area and surface pore area can be done through any number of means which exist in the art, including external heating, steam pyrolysis, or staged pyrolysis, all of which are performed in a temperature range of approximately 400° C. to approximately 900° C. More specifically, the new and improved system and apparatus for the continuous production of biochar (pyrolysis) described in Applicants' copending patent application Ser. No. 13/102,014, incorporated herein by reference in its entirety, may be employed to create the necessary particulate matter which is part of the subject matter of the instant invention. The output of the process described in the '014 application are char and a pyrolysis gas. As described below, the gaseous by products are burned off so that the only outputs aside from the char are water and carbon dioxide. The carbon dioxide released is only a fraction of the carbon dioxide used in the reaction to create the biomass. Accordingly, the process does not create an environmental hazard.

The gas is combusted in a thermal oxidizer and the energy released from the biomass during pyrolysis is used to drive the reaction. Therefore, once the reactor is at operating temperature, the process does not require additional heating energy from external fossil fuels and is energetically substantially self-sufficient. Any cost effective method for the creation of biochar or activated carbon would be suitable for the initial step of this process.

Once a particle having the desired composition and surface area has been created, it is important to treat or coat the particle and the particle's surface to create the desired oleophilic properties. The coating step is accomplished by either a chemical or an oxidative activization of a particle. Specifically, the second step of the process of the present invention comprises coating the pyrolyzed material created in the initial process step described above with a non-polar substance such as paraffin to create a bias in the internal surface area towards non-polar absorption over polar absorption. This is most easily done by allowing the produced biochar material to interact with the gases and volatilized hydrocarbon by-products produced in the above-referenced processes in a temperature controlled environment so that a required amount of oleophilic chemicals are permanently adsorbed onto the surface of the biochar via oxidation. The temperature controlled environment hereinabove described may include, by way of example and not of limitation, cooling the pyrolyzed material from the pyrolysis temperature range through approximately 200° C. to ambient temperature in a cooling medium. The cooling medium may include the non-polar substance such as paraffin. The desired surface oleophilic properties previously described are thus created by a process which is energetically substantially self sufficient, does not use any environmentally hazardous products during processing, and does not produce any environmentally hazardous products or byproducts.

It is also possible that a chemical reaction-type process could be used for surface treatment that is not derived from the pyrolysis process. While one method for surface property modification is described, any chemical modification of a produced biochar is, in principle, the same and would give the same effect without departing from the scope of the instant invention.

Following the creation of an environmental remediation material in accordance with the present invention which possesses the desired surface area and surface properties, secondary treatments designed to optimize the material for specific chemical remediation applications may be applied as necessary. By way of example and not of limitation, when treating chemical contamination of a body of water, it may desirable to create a biochar particle of specific density and buoyancy so that it can be deployed at prescribed depths. This can be accomplished through any number of means, including but not limited to the adhesion of the particle onto a heavier dense inert particle or the coating of the particle with a heavier dense inert substance such as clay. Additionally, the large internal surface area of the biochar particle-enables the material to be advantageously modified with a compound designed to break down or otherwise render inert the targeted chemical. The biochar particle also proves ideal for inoculation with microbial organisms which can be selected for their abilities to metabolize a chemical contaminant such as oil or to produce oxygen to counteract the oxygen depletion that is associated with oil plumes and other similar contaminants. By way of example and not of limitation, one such microbial organism with which the remediation material may be inoculated is Alcanivorax, however, other microorganisms may be selected depending upon the desired application.

The Material:

The material described herein has a number of primary and secondary properties and characteristics which make it ideal for chemical remediation in a body of water. The primary properties include:

1. a composition of matter or particle having a large internal surface area created through the pyrolysis of an organic material or biomass;

2. the composition of matter is chemically inert and will not decompose in an aqueous environment;

3. the composition of matter includes greater than approximately 80% carbon so as to avoid a role in an organic carbon cycle;

4. the composition of matter/particle being more oleophilic than hydrophilic so that it is able to adsorb/absorb non-polar molecules such as oil from a polar environment such as water, regardless of the presence or absence of chemical dispersants that have been used to dilute or dissolve the oil;

5. removablitiy/transportablilty/destructability of the particle from the environment following absorption of a contaminant, by way of example by incineration; and 6. environmental compatibility—the particle may be left in the environment where the sequestered chemical can decompose by natural means without disrupting or contaminating the surrounding ecosystem.

The secondary properties describe a composition of matter created through the pyrolysis of an organic material or biomass which has been treated to manage the environmental effects of chemical contamination at a large or small concentration. As hereinabove described in greater detail, these treatments include, but are not limited to the creation of a particle with a specific buoyancy so that it can be deployed to specific depth regions of the a body of water and/or a composition of matter which has been chemically treated or inoculated with microbial organisms which can be selected to break down chemicals that have been absorbed or to produce oxygen to repair the oxygen depleted regions that are caused by oil and chemical spills.

Changes may be made to the foregoing methods, devices and systems without departing from the scope of the present invention. It should be noted that the matter contained in the above description should be interpreted as illustrative and not in a limiting sense. The following claim(s) are intended to cover all generic and specific features described herein as well as statement of the scope of the present invention, which, as a matter of language, might be said to fall there between.

What is claimed is:

1. A material for the removal, remediation, or sequestration of chemical contaminants from aqueous environmental systems comprising:

a composition of matter that includes an organic substance thermally converted and treated to increase oleophilicity.

2. The material as described in claim 1 wherein the composition of matter further includes greater than approximately 80% carbon to avoid a role in an organic carbon cycle.

3. A material as described in claim 1 wherein the composition of matter is chemically inert and will not decompose in an aqueous system.

4. A material as described in claim 1 wherein the composition of matter is free of environmentally hazardous chemicals or compounds.

5. A material as described in claim 1 wherein the composition of matter is configured to sink to a desired depth in water through densification or mixing with a dense, inert material.

6. A material as described in claim 5 wherein the dense, inert material comprises clay.

7. A material as described in claim 1 wherein the composition of matter is inoculated with organisms to assist in a biological breakdown of targeted chemicals to prevent readmission of the targeted chemicals into the environment from the composition of matter.

8. A material as described in claim 7, wherein the organisms include Alcanivorax.

9. A material as described in claim 1 wherein the composition of matter is configured for safe incineration after absorbing an oil-based contaminant.

* * * * *